United States Patent
Hanger et al.

(10) Patent No.: US 8,916,751 B2
(45) Date of Patent: *Dec. 23, 2014

(54) CONTROL OF AAD DICOT VOLUNTEERS IN MONOCOT CROPS

(75) Inventors: Gregory A. Hanger, Carmel, IN (US); Andrew E. Robinson, Brownsburg, IN (US); Norbert M. Satchivi, Westfield, IN (US); Richard S. Chambers, Warriewood (AU); Terry R. Wright, Carmel, IN (US)

(73) Assignee: Dow AgroSciences, LLC, Indianapolis, IN (US)

( * ) Notice: Subject to any disclaimer, the term of this patent is extended or adjusted under 35 U.S.C. 154(b) by 130 days.

This patent is subject to a terminal disclaimer.

(21) Appl. No.: 13/511,984

(22) PCT Filed: Nov. 24, 2010

(86) PCT No.: PCT/US2010/057998
§ 371 (c)(1),
(2), (4) Date: Oct. 19, 2012

(87) PCT Pub. No.: WO2011/066382
PCT Pub. Date: Jun. 3, 2011

(65) Prior Publication Data
US 2013/0296170 A1    Nov. 7, 2013

Related U.S. Application Data

(60) Provisional application No. 61/263,950, filed on Nov. 24, 2009, provisional application No. 61/328,942, filed on Apr. 28, 2010.

(51) Int. Cl.
| | |
|---|---|
| *C12N 15/82* | (2006.01) |
| *C12N 15/87* | (2006.01) |
| *A01H 5/00* | (2006.01) |
| *A01N 43/40* | (2006.01) |
| *A01N 43/70* | (2006.01) |
| *A01N 37/40* | (2006.01) |
| *A01N 57/20* | (2006.01) |

(52) U.S. Cl.
CPC ............ *A01N 57/20* (2013.01); *C12N 15/8274* (2013.01); *A01N 43/40* (2013.01); *A01N 43/70* (2013.01); *A01N 37/40* (2013.01)
USPC ............ 800/300; 800/278; 800/298; 800/312

(58) Field of Classification Search
None
See application file for complete search history.

(56) References Cited

U.S. PATENT DOCUMENTS 8,283,522 B2 * 10/2012 Wright et al. ................. 800/300

OTHER PUBLICATIONS

Beckie et al, Herbicide-resistant crops as weeds in North America, CAB Reviews: Perspectives in Agriculture, Veterinary Science, Nutrition and Natural Resources (2007) 2:1-22.*

* cited by examiner

*Primary Examiner* — Cathy Kingdon Worley
*Assistant Examiner* — Mykola Kovalenko
(74) *Attorney, Agent, or Firm* — James Daly; Faegre Baker Daniels LLP

(57) ABSTRACT

The subject invention relates in part to the control of AAD-12 and/or AAD-13 dicot volunteers in fields planted with monocot crops such as corn. The dicots can include soybeans and cotton.

7 Claims, No Drawings

SEQUENCE LISTING

<160> NUMBER OF SEQ ID NOS: 1

<210> SEQ ID NO 1
<211> LENGTH: 10212
<212> TYPE: DNA

<213> ORGANISM: Artificial Sequence
<220> FEATURE:
<223> OTHER INFORMATION: Insert and Flanking squences for Soybean Event
      DAS-68416-4

<400> SEQUENCE: 1

| | | | | | |
|---|---|---|---|---|---|
| ctgtcgttgg | attcacagaa | cattgacgcc | agttttcact | tcgttatctt | tgaattcatt | 60 |
| aaaatcgaat | ctctcaccta | tacccccca | tttttctaat | ccatcataat | caaaattcat | 120 |
| aaatgaatca | gttaccatta | ccataatacc | ttttgaaaa | tgagtttgaa | taatcagtat | 180 |
| ctttagaaaa | ctaattaaga | aattaaataa | aaatattta | tcatgaagat | gagtgtaaga | 240 |
| aaaattatga | aaagtataac | tttatacatt | tctataaaat | tattttttct | tttaatttct | 300 |
| taattaatat | cctaagtaaa | tgagttaata | tttatctttc | aaaaattctt | atagtcgcca | 360 |
| attaattttc | ccatgcaatg | acaacttgtc | cgtattctac | gtggtaggtt | aggctacctg | 420 |
| ccgagacaaa | ttgccttgag | acaaattcaa | tagagaaccc | ttccaaggga | ccattataaa | 480 |
| tagagaactt | tcattaaccg | ataagccaca | cccttcaat | caaacacaaa | cacttgaagt | 540 |
| actaagttag | tgtgtttgag | caaattaact | atggcttcgt | tttgttctag | attgacaatt | 600 |
| tgtttggctc | tgtttgtcct | catatggggg | agtgccaatg | cacaactttc | tacaaacttt | 660 |
| tactaccatt | catgtccaaa | cctcttctcc | tctgtgaaat | ccacagtgca | atctgccata | 720 |
| tctaaggaga | cccgcatggg | tgcttctctc | cttcgcttgt | tcttccacga | ttgctttgtc | 780 |
| aatgtaattt | atttgcacct | tctcccactt | acatacaaat | atgctaagct | tacatatagc | 840 |
| tcctctttct | accacttgca | tgcatcatct | aatttttgttt | gaaacaacac | ttgttccttt | 900 |
| tattatacac | atcatctttg | ataaaatttt | gtcgtgtgca | acttttttt | agtgtgttaa | 960 |
| tcagttctat | gatgatacta | ttagttaaga | aattttaatg | cacttaataa | accattttaa | 1020 |
| gtactttaac | cgttcaatga | tattatatat | ttaaagataa | taaatatttc | tgcttttgtt | 1080 |
| tctatattag | tgtagttaag | aaccttctta | cttcttagct | agctaaatat | taatgagtaa | 1140 |
| acattaacaa | atgcagggat | gtgatggttc | aattctattg | gatgacacat | caagcttcac | 1200 |
| cggagagaag | aacgcaaacc | ccaacaggaa | ctctgctcgt | ggattcgagg | ttattgacaa | 1260 |
| cattaaatca | gccgtggaga | aagtgtgtcc | aggagttgtt | tcctgcgcag | atatccttgc | 1320 |
| catcgctgcc | agagactctg | ttcagattgt | aagtggtcaa | acaaccaaca | aaaacacatt | 1380 |
| aaactaaatc | attaaattgt | acatatcaaa | attaattacc | aatttagtac | cacacatgca | 1440 |
| attaaagaga | acattttgtt | gattttgatc | aatatagctt | ggaggcccta | catggaatgt | 1500 |
| taaacttgga | agaagagacg | ctagaactgc | tagccaatct | gctgctaaca | atggcatccc | 1560 |
| tgcacccact | tcaaacctta | accaactcat | ctcaagattt | agcgctcttg | gactttccac | 1620 |
| caaggacttg | gtcgccttgt | ccggtacaaa | acatatatca | cataattttc | caattaatta | 1680 |
| catttcaatc | atatagtaaa | atttctcaat | taattaggaa | catgagaaac | ttatagtcac | 1740 |
| acgttcttt | gttgaggaat | attgcatggt | ttaattttgc | tttcattagg | tggtcacaca | 1800 |
| attggacaag | caaggtgcac | aaacttcaga | gcccgcatct | acaacgagac | caacatagaa | 1860 |
| accgcatttg | caaggactag | gcagcaaagc | tgccctagaa | catcagggtc | aggggacaac | 1920 |
| aatctggcac | cacttgatct | tcaaactcca | accagctttg | acaactacta | cttcaagaac | 1980 |
| ctcgttcaga | agaagggtct | cctccactct | gatcagcaac | tgttcaacgg | tgggtccacc | 2040 |
| gactccattg | tgcgtggcta | cagcaccaac | ccgggcacct | tctcctctga | tttcgccgcc | 2100 |
| gccatgatca | agatgggaga | cattagtcct | ctcactggct | ccaatggaga | aatcaggaag | 2160 |

```
aattgtagaa ggattaacta atttgattca gtcttgaata ttaagggtcc tacacatacg    2220
caagcaattt aattgtgttt aataagttgt taaaacatgt tttggttgta ttttggattc    2280
ctagtgtagt ttcggtgatc aatgccgtct actttagtgt gttctacttc cctttatttt    2340
tgtttctttt ttactttttc cttaactata ttgtaggaaa aaaaaaatcc tttatcaagc    2400
atttatcaag aacggagttt gcttttaat tttcccttca taacattcca tcagaattca    2460
gttttgcttt tgcttctaaa ttacgttcaa atcagggatg ataatcggtt aggtaatata    2520
tacagtaccc cttgcatagt cacgtttgaa aaatataatc atacttagtt cggtaacaat    2580
ttaaattatc attctcgtaa tcattagcta cttatgcact catatccgta tccgctactt    2640
gctcttgtcg taagtcaata aattaatata aaaaaatact taaaacttgt tacaactaaa    2700
ttaaaaattt attttaaat cattcaagca ccagtcagca tcatcacacc aaaagttagg    2760
cccgaatagt ttgaaattag aaagctcgca attgaggtct acaggccaaa ttcgctctta    2820
gccgtacaat attactcacc ggatcctaac cggtgtgatc atgggccgcg attaaaaatc    2880
tcaattatat ttggtctaat ttagtttggt attgagtaaa acaaattcga accaaaccaa    2940
aatataaata tatagttttt atatatatgc ctttaagact ttttatagaa ttttctttaa    3000
aaaatatcta gaaatatttg cgactcttct ggcatgtaat atttcgttaa atatgaagtg    3060
ctccattttt attaacttta aataattggt tgtacgatca ctttcttatc aagtgttact    3120
aaaatgcgtc aatctctttg ttcttccata ttcatatgtc aaaacctatc aaaattctta    3180
tatatctttt tcgaatttga agtgaaattt cgataattta aaattaaata gaacatatca    3240
ttatttaggt atcatattga tttttatact taattactaa atttggttaa ctttgaaagt    3300
gtacatcaac gaaaaattag tcaaacgact aaaataaata aatatcatgt gttattaaga    3360
aaattctcct ataagaatat tttaatagat catatgtttg taaaaaaat taattttac     3420 taacacatat atttacttat caaaaatttg acaagtaag attaaaataa tattcatcta    3480
acaaaaaaaa aaccagaaaa tgctgaaaac ccggcaaaac cgaaccaatc caaaccgata    3540
tagttggttt ggtttgattt tgatataaac cgaaccaact cggtccattt gcaccctaa    3600 tcataatagc tttaatattt caagatatta ttaagttaac gttgtcaata tcctggaaat    3660
tttgcaaaat gaatcaagcc tatatggctg taatatgaat ttaaaagcag ctcgatgtgg    3720
tggtaatatg taatttactt gattctaaaa aaatatccca agtattaata atttctgcta    3780
ggaagaaggt tagctacgat ttacagcaaa gccagaatac aatgaaccat aaagtgattg    3840
aagctcgaaa tatacgaagg aacaaatatt tttaaaaaa tacgcaatga cttggaacaa    3900
aagaaagtga tatatttttt gttcttaaac aagcatcccc tctaaagaat ggcagttttc    3960
ctttgcatgt aactattatg ctcccttcgt tacaaaaatt ttggactact attgggaact    4020
tcttctgaaa atagtggcca ccgcttaatt aaggcgcgcc atgcccgggc aagcggccgc    4080
acaagtttgt acaaaaaagc aggctccgcg tgactgact gaaaagcttg tcgacctgca    4140
ggtcaacgga tcaggatatt cttgtttaag atgttgaact ctatggaggt ttgtatgaac    4200
tgatgatcta ggaccggata agttcccttc ttcatagcga acttattcaa agaatgtttt    4260
gtgtatcatt cttgttacat tgttattaat gaaaaaatat tattggtcat tggactgaac    4320
acgagtgtta aatatggacc aggccccaaa taagatccat tgatatatga attaaataac    4380
aagaataaat cgagtcacca aaccacttgc cttttttaac gagacttgtt caccaacttg    4440
atacaaaagt cattatccta tgcaaatcaa taatcataca aaaatatcca ataacactaa    4500
aaaattaaaa gaaatggata atttcacaat atgttatacg ataaagaagt tacttttcca    4560
```

```
agaaattcac tgattttata agcccacttg cattagataa atggcaaaaa aaaacaaaaa      4620
ggaaaagaaa taaagcacga agaattctag aaaatacgaa atacgcttca atgcagtggg      4680
acccacggtt caattattgc caattttcag ctccaccgta tatttaaaaa ataaaacgat      4740
aatgctaaaa aaatataaat cgtaacgatc gttaaatctc aacggctgga tcttatgacg      4800
accgttagaa attgtggttg tcgacgagtc agtaataaac ggcgtcaaag tggttgcagc      4860
cggcacacac gagtcgtgtt tatcaactca aagcacaaat acttttcctc aacctaaaaa      4920
taaggcaatt agccaaaaac aactttgcgt gtaaacaacg ctcaatacac gtgtcatttt      4980
attattagct attgcttcac cgccttagct ttctcgtgac ctagtcgtcc tcgtcttttc      5040
ttcttcttct tctataaaac aatacccaaa gcttcttctt cacaattcag atttcaattt      5100
ctcaaaatct taaaaacttt ctctcaattc tctctaccgt gatcaaggta aatttctgtg      5160
ttccttattc tctcaaaatc ttcgattttg ttttcgttcg atcccaattt cgtatatgtt      5220
ctttggttta gattctgtta atcttagatc gaagacgatt ttctgggttt gatcgttaga      5280
tatcatctta attctcgatt agggtttcat aaatatcatc cgatttgttc aaataatttg      5340
agttttgtcg ataattact cttcgatttg tgatttctat ctagatctgg tgttagtttc      5400
tagtttgtgc gatcgaattt gtcgattaat ctgagttttt ctgattaaca gagatctcca      5460
tggctcagac cactctccaa atcacaccca ctggtgccac cttgggtgcc acagtcactg      5520
gtgttcacct tgccacactt gacgatgctg gtttcgctgc cctccatgca gcctggcttc      5580
aacatgcact cttgatcttc cctgggcaac acctcagcaa tgaccaacag attacctttg      5640
ctaaacgctt tggagcaatt gagaggattg gcggaggtga cattgttgcc atatccaatg      5700
tcaaggcaga tggcacagtg cgccagcact ctcctgctga gtgggatgac atgatgaagg      5760
tcattgtggg caacatggcc tggcacgccg actcaaccta catgccagtc atggctcaag      5820
gagctgtgtt cagcgcagaa gttgtcccag cagttggggg cagaacctgc tttgctgaca      5880
tgagggcagc ctacgatgcc cttgatgagg caacccgtgc tcttgttcac caaaggtctg      5940
ctcgtcactc ccttgtgtat tctcagagca agttgggaca tgtccaacag gccgggtcag      6000
cctacatagg ttatggcatg gacaccactg caactcctct cagaccattg gtcaaggtgc      6060
atcctgagac tggaaggccc agcctcttga tcggccgcca tgcccatgcc atccctggca      6120
tggatgcagc tgaatcagag cgcttccttg aaggacttgt tgactgggcc tgccaggctc      6180
ccagagtcca tgctcaccaa tgggctgctg gagatgtggt tgtgtgggac aaccgctgtt      6240
tgctccaccg tgctgagccc tgggatttca agttgccacg tgtgatgtgg cactccagac      6300
tcgctggacg cccagaaact gagggtgctg ccttggtttg agtagttagc ttaatcacct      6360
agagctcggt caccagcata atttttatta atgtactaaa ttactgtttt gttaaatgca      6420 attttgctttt ctcgggattt taatatcaaa atctatttag aaatacacaa tattttgttg      6480
caggcttgct ggagaatcga tctgctatca taaaaattac aaaaaaattt tatttgcctc      6540
aattatttta ggattggtat taaggacgct taaattattt gtcgggtcac tacgcatcat      6600
tgtgattgag aagatcagcg atacgaaata ttcgtagtac tatcgataat ttatttgaaa      6660
attcataaga aaagcaaacg ttacatgaat tgatgaaaca atacaaagac agataaagcc      6720
acgcacattt aggatattgg ccgagattac tgaatattga gtaagatcac ggaatttctg      6780
acaggagcat gtcttcaatt cagcccaaat ggcagttgaa atactcaaac cgccccatat      6840
gcaggagcgg atcattcatt gtttgtttgg ttgcctttgc caacatggga gtccaaggtt      6900
```

```
gcggccgcgc gccgacccag ctttcttgta caaagtggtt gcggccgctt aattaaattt    6960
aaatgcccgg gcgtttaaac gcggccgctt aattaaggcc ggcctgcagc aaacccagaa    7020
ggtaattatc caagatgtag catcaagaat ccaatgttta cgggaaaaac tatggaagta    7080
ttatgtaagc tcagcaagaa gcagatcaat atgcggcaca tatgcaacct atgttcaaaa    7140
atgaagaatg tacagataca agatcctata ctgccagaat acgaagaaga atacgtagaa    7200
attgaaaaag aagaaccagg cgaagaaaag aatcttgaag acgtaagcac tgacgacaac    7260
aatgaaaaga agaagataag gtcggtgatt gtgaaagaga catagaggac acatgtaagg    7320
tggaaaatgt aagggcggaa agtaacctta tcacaaagga atcttatccc ccactactta    7380
tccttttata ttttttccgtg tcatttttgc ccttgagttt tcctatataa ggaaccaagt    7440
tcggcatttg tgaaaacaag aaaaaatttg tgtaagcta ттттсттттga agtactgagg    7500 atacaacttc agagaaatt gtaagtttgt agatctccat gtctccggag aggagaccag    7560

ttgagattag gccagctaca gcagctgata tggccgcggt ttgtgatatc gttaaccatt    7620
acattgagac gtctacagtg aactttagga cagagccaca acaccacaa gagtggattg    7680 atgatctaga gaggttgcaa gatagatacc cttggttggt tgctgaggtt gagggtgttg    7740

tggctggtat tgcttacgct gggccctgga aggctaggaa cgcttacgat tggacagttg    7800
agagtactgt ttacgtgtca cataggcatc aaaggttggg cctaggatcc acattgtaca    7860
cacatttgct taagtctatg gaggcgcaag gttttaagtc tgtggttgct gttataggcc    7920

ttccaaacga tccatctgtt aggttgcatg aggctttggg atacacagcc cggggtacat    7980

tgcgcgcagc tggatacaag catggtggat ggcatgatgt tggtttttgg caaagggatt    8040

ttgagttgcc agctcctcca aggccagtta ggccagttac ccagatctga ggtaccctga    8100
gcttgagctt atgagcttat gagcttagag ctcggatcca ctagtaacgg ccgccagtgt    8160
gctggaattc gcccttgact agataggcgc ccagatcggc ggcaatagct tcttagcgcc    8220
atcccgggtt gatcctatct gtgttgaaat agttgcggtg ggcaaggctc tctttcagaa    8280
agacaggcgg ccaaaggaac ccaaggtgag gtgggctatg gctctcagtt ccttgtggaa    8340
gcgcttggtc taaggtgcag aggtgttagc gggatgaagc aaaagtgtcc gattgtaaca    8400
agatatgttg atcctacgta aggatattaa agtatgtatt catcactaat ataatcagtg    8460

tattccaata tgtactacga ttccaatgt ctttattgtc gccgtatgta atcggcgtca    8520
caaaataatc cccggtgact ttcttttaat ccaggatgaa ataatatgtt attataattt    8580

ttgcgatttg gtccgttata ggaattgaag tgtgcttgcg gtcgccacca ctcccatttc    8640 aтaaтттттас atgtatttga aaaataaaaa tttatggtat tcaatttaaa cacgtatact    8700

tgtaaagaat gatatcttga aagaaatata gtttaaatat ttattgataa ataacaagt    8760 caggtattat agtccaagca aaaacataaa tttattgatg caagtttaaa ttcagaaata    8820

ttcaataac tgattatatc agctggtaca ttgccgtaga tgaaagactg agtgcgatat    8880

tatggtgtaa tacatagcgg ccgggtttct agtcaccggt taggatccgt ttaaactcga    8940
ggctagcgca tgcacataga cacacacatc atctcattga tgcttggtaa taattgtcat    9000

tagattgttt ttatgcatag atgcactcga aatcagccaa ttttagacaa gtatcaaacg    9060
gatgtgactt cagtacatta aaaacgtccg caatgtgtta ttaagttgtc taagcgtcaa    9120

tattttaatt cttaacaatc aatattttaa ттcтттaaacт ttattaaatc taacaataaa    9180
ctgtaagaac taattcttaa acttcaataa acaatactgc gтттттagтaa ttaaattaat    9240 aatatataga tatagatata тaaттттgтca acatattctt acстaтттттт ccattgaaat    9300
```

```
atgttagcaa gttcaaaaaa agttttgaca aaaaactcta ctatcttttg tttcatttac    9360
tttatgtgag ggatataata gtaatataac atttagttta tttaaagaaa ataaaaaagt    9420
taatttctct ttctgccact gatactctat ggtggagaga tccgatgcag tggtggagcc    9480
tggcctcgac acataagtgt gacgacgcag ctgttgaaga gatctgattc gacggtgggg    9540
taatgcatgg tggttgacag gttgatgggt ggagaagacg taattgctac cgccgtcaac    9600
ggaggaagga gcaaagatgt ctcgtatgtg aaaattatgc ggttgagatg ccgtttcatt    9660 cccttttaaaa aaatcccttg atggttgcaa tgcaaattaa aaattgaaaa aataattaat    9720
tgttcaaatt aaagatttag catgaaaaaa aaaacactta attgtgccca tgactccatg    9780
acctgcgtaa cttgggaagg aaaggaattt ttttgctaaa ggaaggcatg ggaagatgag    9840
agaggagaga gaatcagtgg aagtgagaga aattaacttt ttgttttta aaaactaaat     9900 attatattac tattatatat atatatatat atatataaaa gatttttag ctggattctt     9960 gatataaaaa atttctcacc atatttatta ttatatattt ttttggagat ctcaaaaaag    10020
gaagttggat ttcttctcaa taactctaaa aaattattcc tatttcaaaa aatattttt     10080 atgtctttct ctaattgatg aataatatct atttaagtat attttattgt gaaatccaca    10140
aaagtgactg ataaatctaa tttaggatct accattagag aaaaataaat aaattcttat    10200
attatatgtg at                                                       10212
```

CONTROL OF AAD DICOT VOLUNTEERS IN MONOCOT CROPS

CROSS-REFERENCE TO RELATED APPLICATIONS

This application is a national phase application, filed pursuant to 35 U.S.C. §371, of PCT application No. PCT/US2010/057998, filed on Nov. 24, 2010, which claims the benefit of U.S. Provisional Application No. 61/263,950, filed on Nov. 24, 2009 and U.S. Provisional Application No. 61/328,942, filed on Apr. 28, 2010. The prior applications are incorporated herein by reference in their entirety.

BACKGROUND

Corn (monocot) and soybeans (dicot), for example, can be rotated in various crop rotation cycles in various geographies. Cotton is also a dicot.

"Volunteer" plants are unwanted plants from the prior growing season that emerge in a field planted with crops for the current growing season. Volunteers are basically weeds, and can, like weeds, reduce harvest and yield of the crop of interest for the current growing season. The volunteers divert fertilizer resources and the like from the desired crops.

Unlike plain weeds, volunteers are often specifically engineered to be resistant to some herbicides. Thus, controlling volunteers can be more difficult than controlling naturally occurring weeds.

AAD (aryloxy alkanoate dioxygenase) genes as described herein impart high levels of tolerance to 2,4-D herbicides in plants that are transformed with an AAD gene.

AAD-1 genes also impart high levels of tolerance to phenoxy- and aryloxyphenoxyproplonate herbicides ("fops" such as fluazifop and haloxyfop). (AAD-1 genes are described in WO 2007/053482.) Thus, AAD-1 allows the use of some fops as either selection agents or as herbicides on crops where crop destruction would be expected without the AAD-1 gene.

AAD-12 and AAD-13 genes also impart high levels of tolerance to pyridyloxyacetate herbicides (such as triclopyr and fluroxypyr; "pyrs") to soybeans and other dicot species transformed with the gene. Thus, AAD-12 and AAD-13 each allow the use of pyrs as either selection agents or as herbicides on crops where crop destruction would be expected without the AAD-12 or AAD-13 gene.

There are very numerous dicot-only herbicides that kill dicots, or selective dicots.

BRIEF SUMMARY

The subject invention relates in part to the control of AAD-12 and/or AAD-13 dicot volunteers in fields planted with monocot crops such as corn. The dicots can include soybeans and cotton.

The subject invention also relates in part to the recognition that one potential downside to the use of AAD genes is that volunteers can be resistant to 2,4-D, as well as to pyrs (in the case of AAD-12 and AAD-13). Thus, in the case of AAD-12 or -13, pyr herbicides will no longer be effective for control of these volunteer AAD soybeans or cotton, for example, in fields planted with monocots such as corn. The subject invention relates in part to the recognition that when an AAD gene is stacked in dicots with other herbicide resistance traits (such as glyphosate, glufosinate, and the like), control of any resulting volunteer dicot plants in the following year can be an issue.

According to the subject invention, dicamba is selected, from almost innumerable other options, as being useful according to the subject invention for the control of volunteer AAD (such as AAD-12) dicot plants in a corn field.

In other embodiments, clopyralid is used for the control of volunteer AAD (such as AAD-12) dicot plants in a corn field.

Corn is naturally tolerant to both dicamba and clopyralid.

Yet another option for controlling volunteer AAD (such as AAD-12) dicots is triazines such as atrazine.

Another option according to the subject invention is if the dicots of the previous season were susceptible to either glyphosate or glufosinate, and the corn crop is tolerant to glyphosate or glufosinate, then glyphosate or glufosinate, respectively, could be used to control the dicot volunteers. Glyphosate could accordingly be used in a field of ROUND UP READY corn. Glufosinate could accordingly be used in a field of LIBERTY LINK corn. If the dicots of the previous season were susceptible to both glyphosate and glufosinate (that is, if the dicots did not have either resistance trait), and the corn crop is tolerant to both glyphosate and glufosinate, then either glyphosate or glufosinate or both could be used to control the dicot volunteers.

If the dicot (such as soy), however, comprises a PAT gene, for example, this would preclude the use of glufosinate to control the dicot volunteers (as the dicot PAT volunteers would tolerate glufosinate).

DETAILED DESCRIPTION

As used herein and unless otherwise specified, preferred dicots are soybeans or cotton.

One aspect of the subject invention includes the use of dicamba herbicides to remove volunteer AAD-12 or -13 dicots in a field of monocots, such as corn.

In some specific embodiments, the AAD-12 is present in soybeans as the AAD-12 soy event designated DAS-68416-4 having seed deposited with American Type Culture Collection (ATCC) with Accession No. PTA-10442, and progeny derived thereof. 2500 seeds were deposited in accordance with the Budapest Treaty on Oct. 22, 2009. The deposit was tested on Nov. 2, 2009, and on that date, the seeds were viable. Such events are disclosed in U.S. Ser. No. 61/263,950 (filed Nov. 24, 2009). Such AAD-12 dicot volunteers could be present in the following year's corn fields. Thus, the subject invention includes the application of a dicamba (or other as disclosed herein) herbicide to volunteer AAD-12 soy plants, particularly where the soybean plant comprises the 68416-4 event. Such "416" event plants comprise SEQ ID NO:1. AAD-12 protein sequences can be found in WO 2007/053482 (SEQ ID NO:2 and SEQ ID NO:4). AAD-13 protein sequences can be found in WO 2008/141154 (SEQ ID NO:2 and SEQ ID NO:4). Sequences for use in accordance with the subject invention can have at least 75%, 80%, 85%, 90%, 95%, or 99%, for example, sequence identity with any of these sequences.

Because of the specific detoxifying aspects of AAD genes, dicamba herbicides applied to corn fields would not be subject to detoxification by the AAD gene of the dicot volunteers, and AAD-12 or -13 dicot volunteers would remain highly susceptible to the dicamba herbicide.

According to the subject invention, various herbicide chemistries have been carefully selected to provide control of AAD-12 or -13 dicots as detailed herein. For example, when an AAD-12 or -13 gene was used alone in the previous season's dicot (such as soybeans), dicamba, clopyralid, atrazines, glyphosate, and/or glufosinate could be used to control volunteer AAD soybeans (or cotton), assuming that the soybeans (or other dicots) were naturally or engineered to be resistant to any of these herbicides.

That is, if the volunteer AAD-12 or -13 dicots were also stacked with a glyphosate- or glufosinate-trait, then glufosinate or glyphosate, respectively, could be used in the corn field of the current season, assuming that the corn also has a resistance trait against glufosinate or glyphosate, respectively.

Even if these AAD soybean volunteers possess glyphosate- and glufosinate-tolerance traits, dicamba (and/or the others) could still be used to control those volunteers.

Selection of herbicides to use on the current planted fields, according to the subject invention, can thus depend in part on the herbicide-tolerance trait(s) that were used in the previous season dicot, and on the tolerance trait(s) present in the field of corn (or other monocot) crop of the current growing season. Thus, additional herbicide chemistries can provide control of AAD-12 or -13 dicot volunteers.

In Roundup Ready (or GAT or other glyphosate-tolerant crops) or Liberty Link (or other glufosinate-tolerant crops) corn fields, for example, glyphosate or glufosinate, respectively, can be used to control the AAD dicot volunteers, assuming the dicot volunteers do not also possess that same respective herbicide-tolerance trait. Again, a PAT gene in the soy (or other dicot) would preclude the use of glufosinate for controlling the soy (or other dicot) volunteers.

EXAMPLES

Example 1

Control of Volunteer AAD-12 Soybean in a Field Planted with AAD-1 Corn Using Alternative Herbicides In one embodiment, volunteer transgenic soybean lines containing the AAD-12 expression cassette are controlled within a field of AAD-1 corn by the application of a herbicide or combination of herbicides. The specific herbicide used to control the volunteer transgenic AAD-12 soybean line is dependent upon the type of AAD-1 corn seed being planted within the field (e.g., stacked with Round-up Ready trait, Liberty Link trait, or other herbicide tolerant traits).

Furthermore, the AAD-12 trait may be stacked with other additional herbicide tolerant trait(s) via conventional breeding or a molecular stack. In such an example, the specific herbicide used to control the volunteer AAD-12 soybean stacked with another herbicide tolerant trait(s) will be dependent upon the additional herbicide tolerant trait(s) and the type of AAD-1 corn being planted within the field.

The application of a given herbicide can be made before planting at pre-emergence/burndown or post-emergence after planting to control the volunteer transgenic AAD-12 soybean lines. Table 1 lists the herbicides to be used at the different stages of planting (pre-emergence or post-emergence) to control volunteer transgenic soybean in a field planted with corn containing herbicide tolerant trait(s). Table 2 lists the herbicides to be used at different stages of planting to control volunteer AAD-12 soybean in a field planted with corn containing the AAD-1 herbicide tolerant trait. At or about a 1× Field Rate concentration of herbicide would be applied, as either a tank mix or alone, to the field for both pre-emergent and post-emergent volunteer control.

The control of transgenic soybean plants containing the AAD-12 expression cassette within a field of AAD-1 corn would be applicable for the control of volunteer AAD-12 transgenic dicot plants (including, but not limited too; soybean, cotton, canola, flax, sunflower, legumes, alfalfa, peanut, and tomato) within a field being planted with a monocot crop (including, but not limited too; corn, rice, sugar cane, switch grass, turf grass species, sorghum, barley, wheat, and oats, and durum). The example described above, in which volunteer transgenic AAD-12 soybean plants are controlled in an AAD-1 corn field, is illustrative of the invention and not intended to restrict the scope of this embodiment.

Example 2

Control of Volunteer Soybean (Conventional or Containing Non-AAD Herbicide Tolerance Traits) in a Field Planted with AAD Corn Using Alternative Herbicides In an embodiment, volunteer transgenic soybean lines (containing the Clear Field trait, Roundup Ready or other Glyphosate Tolerant Trait, Liberty Link Trait, Imidazolonine tolerant trait, or any stacked combination thereof) or volunteer conventional soybean lines are controlled within a field of transgenic AAD corn (either AAD-1 or AAD-12) by the application of a herbicide or combination of herbicides. The specific herbicide used to control the volunteer soybean plants is dependent upon the type of soybean seed being planted within the field (e.g., conventional soybean, Roundup Ready Soybean, Liberty Link Soybean, etc.).

Moreover, the specific herbicide used to control the volunteer conventional or transgenic soybean line is dependent upon the type of AAD transgenic corn seed (i.e. stacked traits or alone) being planted within the field and the trait possessed by the volunteer soybean line. For example an AAD-1 transgenic corn line that has been stacked with another herbicide tolerant trait such as PAT could be sprayed with a herbicide mixture containing glufosinate and a combination or single application of fluroxypyr, triclopyr, and/or 2,4-D; but only where the preceding volunteer plants do not contain PAT (or other glufosinate tolerant trait) and AAD-1.

The application of a given herbicide can be made before planting at pre-emergence/burndown or post-emergence after planting to control the volunteer conventional or transgenic soybean lines. Table 3 lists the herbicides to be used at the different stages of planting (pre-emergence or post-emergence) to control volunteer conventional or transgenic soybean. At or about a 1× Field Rate concentration of herbicide would be applied, as either a tank mix or alone, to the field for both pre-emergent and post-emergent volunteer control.

The control of conventional or transgenic soybean plants containing a herbicide tolerant expression cassette within a field of AAD transgenic corn (either stacked with other herbicide tolerant traits or alone) would be applicable for the control of a conventional or herbicide tolerant transgenic dicot plant (including, but not limited too; soybean, cotton, canola, flax, sunflower, legumes, alfalfa, peanut, and tomato) within a field being planted with a AAD transgenic monocot crop (including, but not limited too; corn, rice, sugar cane, switch grass, turf grass species, sorghum, barley, wheat, and oats, and durum). The example described above, in which volunteer conventional or transgenic herbicide tolerant soybean plants are controlled in a field planted with AAD transgenic corn, is illustrative of the invention and not intended to restrict the scope of this embodiment.

TABLE 1

Control of volunteer AAD-12 Soybean (alone or stacked with other HT traits) in HT Corn

| Previous year Soybean hybrid | Current year Corn hybrid being planted | Herbicides option - Burndown/PRE | Herbicides option - POST |
|---|---|---|---|
| | | Appl: alone and tank mixes | |
| AAD-12 | CL Corn<br>RR Corn<br>LL Corn<br>GAT<br>GAT + PAT<br>GAT + ALS<br>GAT + PAT + ALS<br>Dicamba<br>Dicamba + LL<br>Dicamba + RR<br>Dicamba + LL + RR | Glyphosate, glufosinate, isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), glyphosate (only for use with RR and GAT Corn single gene and stacks), glufosinate (only for use with LL corn single gene or stacks), Dicamba (only for use with Dicamba tolerant corn single gene or stacks) |
| AAD-12 + PAT | CL Corn<br>RR Corn<br>LL Corn<br>GAT<br>GAT + PAT<br>GAT + ALS<br>GAT + PAT + ALS<br>Dicamba<br>Dicamba + LL<br>Dicamba + RR<br>Dicamba + LL + RR | Glyphosate, isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), glyphosate (only for use with RR and GAT Corn single gene and stacks), Dicamba (only for use with Dicamba tolerant corn single gene or stacks) |
| AAD-12 + TIPS | CL Corn<br>RR Corn<br>LL Corn<br>GAT<br>GAT + PAT<br>GAT + ALS<br>GAT + PAT + ALS<br>Dicamba<br>Dicamba + LL<br>Dicamba + RR<br>Dicamba + LL + RR | Glufosinate, isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), glufosinate (only for use with LL corn single gene or stacks), Dicamba (only for use with Dicamba tolerant corn single gene or stacks) |
| AAD-12 + AHAS | CL Corn<br>RR Corn<br>LL Corn<br>GAT<br>GAT + PAT<br>GAT + ALS<br>GAT + PAT + ALS<br>Dicamba<br>Dicamba + LL<br>Dicamba + RR<br>Dicamba + LL + RR | Glyphosate, glufosinate, isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), glyphosate (only for use with RR and GAT Corn single gene and stacks), glufosinate (only for use with LL corn single gene or stacks), Dicamba (only for use with Dicamba tolerant corn single gene or stacks) |
| AAD-12 + PAT + TIPS | CL Corn<br>RR Corn<br>LL Corn<br>GAT<br>GAT + PAT<br>GAT + ALS<br>GAT + PAT + ALS<br>Dicamba<br>Dicamba + LL<br>Dicamba + RR<br>Dicamba + LL + RR | Isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), Dicamba (only for use with Dicamba tolerant corn single gene or stacks) |
| AAD-12 + PAT + AHAS | CL Corn<br>RR Corn<br>LL Corn<br>GAT<br>GAT + PAT<br>GAT + ALS<br>GAT + PAT + ALS<br>Dicamba<br>Dicamba + LL<br>Dicamba + RR<br>Dicamba + LL + RR | Glufosinate, isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), glyphosate (only for use with RR and GAT Corn single gene and stacks), Dicamba (only for use with Dicamba tolerant corn single gene or stacks) |
| AAD-12 + GAT | CL Corn<br>RR Corn<br>LL Corn<br>GAT<br>GAT + PAT<br>GAT + ALS<br>GAT + PAT + ALS | Glufosinate, isoxaflutole, atrazine, alachlor, clopyralid, diflufenxopyr, mesotrione, isoxaflutole | Atrazine, clopyralid, diflufenxopyr, mesotrione, glufosinate (only for LL Corn traits), Dicamba (only for use with Dicamba tolerant corn single gene or stacks) |

TABLE 1-continued

Control of volunteer AAD-12 Soybean (alone or stacked with other HT traits) in HT Corn

| Previous year Soybean hybrid | Current year Corn hybrid being planted | Herbicides option - Burndown/PRE | Herbicides option - POST |
|---|---|---|---|
| | Dicamba | | |
| | Dicamba + LL | | |
| | Dicamba + RR | | |
| | Dicamba + LL + RR | | |

Gene and trait footnotes:

GT = any glyphosate specific tolerance trait including Roundup Ready (CP4), TIPS EPSPS (GA21, Glytol, DMMG), Athenix's EPSPS, GAT only without ALS, GOX, glyphosate decarboxylase, etc.

ALS = double mutant ALS gene insensitive to all ALS herbicide chemistries including IMI herbicides.

AAD-1 = Aryloxyalkanoate dioxygenase gene providing tolerance to all commercial phenoxy auxin and all aryloxyphenoxypropionate (fop) herbicides.

AAD-12 = Aryloxyalkanoate dioxygenase gene providing tolerance to phenoxyauxin and pyridyloxyacetic auxin herbicides.

PAT = phosphinothricin acetyltransferase gene providing tolerance to glutamine synthetase inhibitors including, but not limited to, glufosinate. Similar phenotype is provided by genes such as BAR, DSM1, DSM2, et al.

AHAS = imidazolinone specific tolerance gene associated with point mutation at S623 of ALS gene (maize sequence) or equivalent amino acid in other spp (e.g., S653 in *Arabidopsis*).

RR = Roundup Ready trait, implies utility of CP4 gene as commercially deployed either alone or in combination with other genes but imparting glyphosate only tolerance.

CL = Clearfield crops, tolerant by nontransgenic means. Primary tolerance is to imidazolinone class of ALS-inhibiting chemistry with some partial tolerance to specific other herbicides with this mode of action. Use of CL designation is intended to distinguish from transgenic use of the AHAS gene.

LL = Liberty Link trait, implies utility of either PAT or BAR gene as commercially deployed either alone or in combination with other genes but imparting only tolerance to glutamine synthetase inhibitors such as glufosinate.

STS = designates resistance to sulfonylurea herbicide chemistry with use of ALS1 gene.

Herbicide footnotes:

IMI = any imidazolinone herbicide including, but not limited to, imazapyr, imazethapyr, imazamox, imazaquin.

DIMS = cyclohexanedione class of herbicides (dims) including, but not limited to, sethoxydim, clethodim, and for the purposes of this demonstration poinoxaden.

Fops = aryloxyphenoxypropionate herbicides (fops) including, but not limited to, quizalofop, haloxyfop, fenoxaprop, fluazifop, et al., their stereospecific isomers or racemic mixtures, and esters, acid, or salts thereof.

ALS inhibitors = any ALS inhibitor to the exclusion of IMI's for the sake of this demonstration (i.e., sulfonylureas, triazolopyrimidine sulfonanalides, sulfonylaminocarbonyltriazolinone).

HPPD = p-Hydroxyphenyl pyruvate dioxygenase inhibitor class of chemistry including but not limited to mesotrione, sulcotrione, isoxaflutole, and pyrazolynate.

MSMA and DSMA = herbicides from the organoarsenicals chemistry family.

N/A = No suitable options available postemergence.

TABLE 2

Control of volunteer AAD-12 Soybean (alone or stacked with other HT traits) in AAD-1 Corn

| Previous year Soybean hybrid | Current year Corn hybrid being planted | Herbicides option - Burndown/PRE | Herbicides option - POST |
|---|---|---|---|
| | Appl: alone and tank mixes | | |
| AAD-12 | AAD-1<br>AAD-1 + PAT<br>AAD-1 + GT<br>AAD-1 + GAT + ALS<br>AAD-1 + AHAS<br>AAD-1 + CL<br>AAD-1 + PAT + GT<br>AAD-1 + PAT + GAT + ALS<br>AAD-1 + PAT + AHAS | Glyphosate, glufosinate, isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), glyphosate (only for use with RR and GAT Corn single gene and stacks), glufosinate (only for use with LL corn single gene or stacks) |
| AAD-12 + PAT | AAD-1<br>AAD-1 + PAT<br>AAD-1 + GT<br>AAD-1 + GAT + ALS<br>AAD-1 + AHAS<br>AAD-1 + CL<br>AAD-1 + PAT + GT<br>AAD-1 + PAT + GAT + ALS<br>AAD-1 + PAT + AHAS | Glyphosate, isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), glyphosate (only for use with RR and GAT Corn single gene and stacks) |
| AAD-12 + TIPS | AAD-1<br>AAD-1 + PAT<br>AAD-1 + GT<br>AAD-1 + GAT + ALS<br>AAD-1 + AHAS<br>AAD-1 + CL<br>AAD-1 + PAT + GT<br>AAD-1 + PAT + GAT + ALS<br>AAD-1 + PAT + AHAS | Glufosinate, isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), glufosinate (only for use with LL corn single gene or stacks) |
| AAD-12 + AHAS | AAD-1<br>AAD-1 + PAT<br>AAD-1 + GT<br>AAD-1 + GAT + ALS<br>AAD-1 + AHAS<br>AAD-1 + CL | Glyphosate, glufosinate, isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), glyphosate (only for use with RR and GAT Corn single gene and |

TABLE 2-continued

Control of volunteer AAD-12 Soybean (alone or stacked with other HT traits) in AAD-1 Corn

| Previous year Soybean hybrid | Current year Corn hybrid being planted | Herbicides option - Burndown/PRE | Herbicides option - POST |
|---|---|---|---|
| | AAD-1 + PAT + GT<br>AAD-1 + PAT + GAT + ALS<br>AAD-1 + PAT + AHAS | (need to be aware of planting restrictions) | stacks), glufosinate (only for use with LL corn single gene or stacks) |
| AAD-12 + PAT + TIPS | AAD-1<br>AAD-1 +<br>AAD-1 + GT<br>AAD-1 + GAT + ALS<br>AAD-1 + AHAS<br>AAD-1 + CL<br>AAD-1 + PAT + GT<br>AAD-1 + PAT + GAT + ALS<br>AAD-1 + PAT + AHAS | Isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions) |
| AAD-12 + PAT + AHAS | AAD-1<br>AAD-1 + PAT<br>AAD-1 + GT<br>AAD-1 + GAT + ALS<br>AAD-1 + AHAS<br>AAD-1 + CL<br>AAD-1 + PAT + GT<br>AAD-1 + PAT + GAT + ALS<br>AAD-1 + PAT + AHAS | Glufosinate, isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), glyphosate (only for use with RR and GAT Corn single gene and stacks) |
| AAD-12 + GAT | AAD-1<br>AAD-1 + PAT<br>AAD-1 + GT<br>AAD-1 + GAT + ALS<br>AAD-1 + AHAS<br>AAD-1 + CL<br>AAD-1 + PAT + GT<br>AAD-1 + PAT + GAT + ALS<br>AAD-1 + PAT + AHAS | Glufosinate, isoxaflutole, atrazine, alachlor, clopyralid, diflufenxopyr, mesotrione, isoxaflutole | Atrazine, clopyralid, diflufenxopyr, mesotrione, glufosinate (only for LL Corn and AAD-1 + PAT based traits) |

Gene and trait footnotes:

GT = any glyphosate specific tolerance trait including Roundup Ready (CP4), TIPS EPSPS (GA21, Glytol, DMMG), Athenix's EPSPS, GAT only without ALS, GOX, glyphosate decarboxylase, etc.
ALS = double mutant ALS gene insensitive to all ALS herbicide chemistries including IMI herbicides.
AAD-1 = Aryloxyalkanoate dioxygenase gene providing tolerance to all commercial phenoxy auxin and all aryloxyphenoxypropionate (fop) herbicides.
AAD-12 = Aryloxyalkanoate dioxygenase gene providing tolerance to phenoxyacetic auxin and pyridyloxyacetic auxin herbicides.
PAT = phosphinothricin acetyltransferase gene providing tolerance to glutamine synthetase inhibitors including, but not limited to, glufosinate. Similar phenotype is provided by genes such as BAR, DSM1, DSM2, et al.
AHAS = imidazolinone specific tolerance gene associated with point mutation at S623 of ALS gene (maize sequence) or equivalent amino acid in other spp (e.g., S653 in *Arabidopsis*).
RR = Roundup Ready trait, implies utility of CP4 gene as commercially deployed either alone or in combination with other genes but imparting glyphosate only tolerance.
CL = Clearfield crops, tolerant by nontransgenic means. Primary tolerance is to imidazolinone class of ALS-inhibiting chemistry with some partial tolerance to specific other herbicides with this mode of action. Use of CL designation is intended to distinguish from transgenic use of the AHAS gene.
LL = Liberty Link trait, implies utility of either PAT or BAR gene as commercially deployed either alone or in combination with other genes but imparting only tolerance to glutamine synthetase inhibitors such as glufosinate.
STS = designates resistance to sulfonylurea herbicide chemistry with use of ALS1 gene.

Herbicide footnotes:

IMI = any imidazolinone herbicide including, but not limited to, imazapyr, imazethapyr, imazamox, imazaquin.
DIMS = cyclohexanedione class of herbicides (dims) including, but not limited to, sethoxydim, clethodim, and for the purposes of this demonstration poinoxaden.
Fops = aryloxyphenoxypropionate herbicides (fops) including, but not limited to, quizalofop, haloxyfop, fenoxaprop, fluazifop, et al., their stereospecific isomers or racemic mixtures, and esters, acid, or salts thereof.
ALS inhibitors = any ALS inhibitor to the exclusion of IMI's for the sake of this demonstration (i.e., sulfonylureas, triazolopyrimidine sulfonanalides, sulfonylaminocarbonyltriazolinone).
HPPD = p-Hydroxyphenyl pyruvate dioxygenase inhibitor class of chemistry including but not limited to mesotrione, sulcotrione, isoxaflutole, and pyrazolynate.
MSMA and DSMA = herbicides from the organoarsenicals chemistry family.
N/A = No suitable options available postemergence.

TABLE 3

Control of volunteer Soybean (alone or stacked with other Herbicide Tolerant traits) in AAD-1-based Corn

| Previous year Soybean hybrid | Current year Corn hybrid being planted | Herbicides option - Burndown/PRE | Herbicides option - POST |
|---|---|---|---|
| | | Appl: alone and tank mixes | |
| CL | AAD-1<br>AAD-1 + PAT<br>AAD-1 + TIPS<br>AAD-1 + AHAS<br>AAD-1 + PAT + TIPS<br>AAD-1 + PAT + AHAS | Glyphosate, glufosinate, bromoxynil, metribuzin, clomazone, flufenacet, s-metolachlor + fomesafen, pendimethalin, ALS herbicides not recommended for soybeans (need to be aware of planting restrictions): | 2,4-D, HPPD<br>2,4-D, HPPD, glufosinate<br>2,4-D, HPPD, glyphosate<br>2,4-D, HPPD<br>2,4-D, HPPD, glufosinate, glyphosate<br>2,4-D, HPPD, glufosinate |

TABLE 3-continued

Control of volunteer Soybean (alone or stacked with other Herbicide Tolerant traits) in AAD-1-based Corn

| Previous year Soybean hybrid | Current year Corn hybrid being planted | Herbicides option - Burndown/PRE | Herbicides option - POST |
|---|---|---|---|
| | AAD-1 + GAT | tribenuron, nicosulfuron, rimsulfuron | 2,4-D, HPPD, glyphosate, ALS herbicides (sulfonylureas, triazolopyrimidine sulfonanalides, sulfobylamino carbonyl triazolinones) except imazaquin, imazpyr, imazamox, imazethapyr, chlorimuron, thifensulfuron |
| RR | AAD-1<br>AAD-1 + PAT<br>AAD-1 + TIPS<br>AAD-1 + AHAS<br>AAD-1 + PAT + TIPS<br>AAD-1 + PAT + AHAS<br>AAD-1 + GAT | Glufosinate, bromoxynil, metribuzin, clomazone, flufenacet, s-metolachlor + fomesafen, pendimethalin, ALS herbicides not recommended for soybeans (need to be aware of planting restrictions): tribenuron, nicosulfuron, rimsulfuron | 2,4-D, HPPD<br>2,4-D, HPPD, glufosinate<br>2,4-D, HPPD<br>2,4-D, HPPD<br>2,4-D, HPPD, glufosinate<br>2,4-D, HPPD, glufosinate<br>2,4-D, HPPD, ALS herbicides (sulfonylureas, triazolopyrimidine sulfonanalides, sulfobylamino carbonyl triazolinones) except imazaquin, imazpyr, imazamox, imazethapyr, chlorimuron, thifensulfuron |
| LL | AAD-1<br>AAD-1 + PAT<br>AAD-1 + TIPS<br>AAD-1 + AHAS<br>AAD-1 + PAT + TIPS<br>AAD-1 + PAT + AHAS<br>AAD-1 + GAT | Glyphosate, bromoxynil, metribuzin, clomazone, flufenacet, s-metolachlor + fomesafen, pendimethalin, ALS herbicides not recommended for soybeans (need to be aware of planting restrictions): tribenuron, nicosulfuron, rimsulfuron | 2,4-D, HPPD<br>2,4-D, HPPD<br>2,4-D, HPPD, glyphosate<br>2,4-D, HPPD<br>2,4-D, HPPD, glyphosate<br>2,4-D, HPPD<br>2,4-D, HPPD, glyphosate, ALS herbicides (sulfonylureas, triazolopyrimidine sulfonanalides, sulfobylamino carbonyl triazolinones) except imazaquin, imazpyr, imazamox, imazethapyr, chlorimuron, thifensulfuron |
| GAT | AAD-1<br>AAD-1 + PAT<br>AAD-1 + TIPS<br>AAD-1 + AHAS<br>AAD-1 + PAT + TIPS<br>AAD-1 + PAT + AHAS<br>AAD-1 + GAT | Glufosinate, bromoxynil, metribuzin, clomazone, flufenacet, s-metolachlor + fomesafen, pendimethalin | 2,4-D, HPPD<br>2,4-D, HPPD, glufosinate<br>2,4-D, HPPD<br>2,4-D, HPPD<br>2,4-D, HPPD, glufosinate<br>2,4-D, HPPD, glufosinate<br>2,4-D, HPPD |
| HPPD | AAD-1<br>AAD-1 + PAT<br>AAD-1 + TIPS<br>AAD-1 + AHAS<br>AAD-1 + PAT + TIPS<br>AAD-1 + PAT + AHAS<br>AAD-1 + GAT | Glyphosate, glufosinate, bromoxynil, metribuzin, clomazone, flufenacet, s-metolachlor + fomesafen, pendimethalin, ALS herbicides not recommended for soybeans (need to be aware of planting restrictions): tribenuron, nicosulfuron, rimsulfuron | 2,4-D<br>2,4-D, glufosinate<br>2,4-D, glyphosate<br>2,4-D<br>2,4-D, glufosinate, glyphosate<br>2,4-D, glufosinate<br>2,4-D, glyphosate, ALS herbicides (sulfonylureas, triazolopyrimidine sulfonanalides, sulfobylamino carbonyl triazolinones) except imazaquin, imazpyr, imazamox, imazethapyr, chlorimuron, thifensulfuron |
| Dicamba | AAD-1<br>AAD-1 + PAT<br>AAD-1 + TIPS<br>AAD-1 + AHAS<br>AAD-1 + PAT + TIPS<br>AAD-1 + PAT + AHAS<br>AAD-1 + GAT | Glyphosate, glufosinate, bromoxynil, metribuzin, clomazone, flufenacet, s-metolachlor + fomesafen, pendimethalin, ALS herbicides not recommended for soybeans (need to be aware of planting restrictions): tribenuron, nicosulfuron, rimsulfuron | 2,4-D, HPPD<br>2,4-D, HPPD, glufosinate<br>2,4-D, HPPD, glyphosate<br>2,4-D, HPPD<br>2,4-D, HPPD, glufosinate, glyphosate<br>2,4-D, HPPD, glufosinate<br>2,4-D, HPPD, glyphosate, ALS herbicides (sulfonylureas, triazolopyrimidine sulfonanalides, sulfobylamino carbonyl triazolinones) except imazaquin, imazpyr, imazamox, imazethapyr, chlorimuron, thifensulfuron |
| Dicamba + RR | AAD-1<br>AAD-1 + PAT<br>AAD-1 + TIPS<br>AAD-1 + AHAS<br>AAD-1 + PAT + TIPS<br>AAD-1 + PAT + AHAS<br>AAD-1 + GAT | glufosinate, bromoxynil, metribuzin, clomazone, flufenacet, s-metolachlor + fomesafen, pendimethalin, ALS herbicides not recommended for soybeans (need to be aware of planting restrictions): tribenuron, nicosulfuron, rimsulfuron | 2,4-D, HPPD<br>2,4-D, HPPD, glufosinate<br>2,4-D, HPPD<br>2,4-D, HPPD<br>2,4-D, HPPD, glufosinate<br>2,4-D, HPPD, glufosinate<br>2,4-D, HPPD, ALS herbicides (sulfonylureas, triazolopyrimidine sulfonanalides, sulfobylamino carbonyl |

TABLE 3-continued

Control of volunteer Soybean (alone or stacked with other Herbicide Tolerant traits) in AAD-1-based Corn

| Previous year Soybean hybrid | Current year Corn hybrid being planted | Herbicides option - Burndown/PRE | Herbicides option - POST |
|---|---|---|---|
| Dicamba + LL + RR | AAD-1<br>AAD-1 + PAT<br>AAD-1 + TIPS<br>AAD-1 + AHAS<br>AAD-1 + PAT + TIPS<br>AAD-1 + PAT + AHAS<br>AAD-1 + GAT | bromoxynil, metribuzin, clomazone, flufenacet, s-metolachlor + fomesafen, pendimethalin, ALS herbicides not recommended for soybeans (need to be aware of planting restrictions): tribenuron, nicosulfuron, rimsulfuron | triazolinones) except imazaquin, imazpyr, imazamox, imazethapyr, chlorimuron, thifensulfuron<br>2,4-D, HPPD<br>2,4-D, HPPD<br>2,4-D, HPPD<br>2,4-D, HPPD<br>2,4-D, HPPD<br>2,4-D, HPPD<br>2,4-D, HPPD, ALS herbicides (sulfonylureas, triazolopyrimidine sulfonanalides, sulfobylamino carbonyl triazolinones) except imazaquin, imazpyr, imazamox, imazethapyr, chlorimuron, thifensulfuron |
| Dicamba + RR + HPPD | AAD-1<br>AAD-1 + PAT<br>AAD-1 + TIPS<br>AAD-1 + AHAS<br>AAD-1 + PAT + TIPS<br>AAD-1 + PAT + AHAS<br>AAD-1 + GAT | glufosinate, bromoxynil, metribuzin, clomazone, flufenacet, s-metolachlor + fomesafen, pendimethalin, ALS herbicides not recommended for soybeans (need to be aware of planting restrictions): tribenuron, nicosulfuron, rimsulfuron | 2,4-D<br>2,4-D, glufosinate<br>2,4-D<br>2,4-D<br>2,4-D, glufosinate<br>2,4-D, glufosinate<br>2,4-D, ALS herbicides (sulfonylureas, triazolopyrimidine sulfonanalides, sulfobylamino carbonyl triazolinones) except imazaquin, imazpyr, imazamox, imazethapyr, chlorimuron, thifensulfuron |
| Dicamba + LL + RR + HPPD | AAD-1<br>AAD-1 + PAT<br>AAD-1 + TIPS<br>AAD-1 + AHAS<br>AAD-1 + PAT + TIPS<br>AAD-1 + PAT + AHAS<br>AAD-1 + GAT | bromoxynil, metribuzin, clomazone, flufenacet, s-metolachlor + fomesafen, pendimethalin, ALS herbicides not recommended for soybeans (need to be aware of planting restrictions): tribenuron, nicosulfuron, rimsulfuron | 2,4-D<br>2,4-D<br>2,4-D<br>2,4-D<br>2,4-D<br>2,4-D<br>2,4-D, ALS herbicides (sulfonylureas, triazolopyrimidine sulfonanalides, sulfobylamino carbonyl triazolinones) except imazaquin, imazpyr, imazamox, imazethapyr, chlorimuron, thifensulfuron |

Gene and trait footnotes:

GT = any glyphosate specific tolerance trait including Roundup Ready (CP4), TIPS EPSPS (GA21, Glytol, DMMG), Athenix's EPSPS, GAT only without ALS, GOX, glyphosate decarboxylase, etc.
ALS = double mutant ALS gene insensitive to all ALS herbicide chemistries including IMI herbicides.
AAD-1 = Aryloxyalkanoate dioxygenase gene providing tolerance to all commercial phenoxy auxin and all aryloxyphenoxypropionate (fop) herbicides.
AAD-12 = Aryloxyalkanoate dioxygenase gene providing tolerance to phenoxyacetic auxin and pyridyloxyacetic auxin herbicides.
PAT = phosphinothricin acetyltransferase gene providing tolerance to glutamine synthetase inhibitors including, but not limited to, glufosinate. Similar phenotype is provided by genes such as BAR, DSM1, DSM2, et al.
AHAS = imidazolonine specific tolerance gene associated with point mutation at S623 of ALS gene (maize sequence) or equivalent amino acid in other spp (e.g., S653 in *Arabidopsis*).
RR = Roundup Ready trait, implies utility of CP4 gene as commercially deployed either alone or in combination with other genes but imparting glyphosate only tolerance.
CL = Clearfield crops, tolerant by nontransgenic means. Primary tolerance is to imidazolinone class of ALS-inhibiting chemistry with some partial tolerance to specific other herbicides with this mode of action. Use of CL designation is intended to distinguish from transgenic use of the AHAS gene.
LL = Liberty Link trait, implies utility of either PAT or BAR gene as commercially deployed either alone or in combination with other genes but imparting only tolerance to glutamine synthetase inhibitors such as glufosinate.
STS = designates resistance to sulfonylurea herbicide chemistry with use of ALS1 gene.

Herbicide footnotes:

IMI = any imidazolinone herbicide including, but not limited to, imazapyr, imazethapyr, imazamox, imazaquin.
DIMS = cyclohexanedione class of herbicides (dims) including, but not limited to, sethoxydim, clethodim, and for the purposes of this demonstration poinoxaden.
Fops = aryloxyphenoxypropionate herbicides (fops) including, but not limited to, quizalofop, haloxyfop, fenoxaprop, fluazifop, et al., their stereospecific isomers or racemic mixtures, and esters, acid, or salts thereof.
ALS inhibitors = any ALS inhibitor to the exclusion of IMI's for the sake of this demonstration (i.e., sulfonylureas, triazolopyrimidine sulfonanalides, sulfonylaminocarbonyltriazolinone).
HPPD = p-Hydroxyphenyl pyruvate dioxygenase inhibitor class of chemistry including but not limited to mesotrione, sulcotrione, isoxaflutole, and pyrazolynate.
MSMA and DSMA = herbicides from the organoarsenicals chemistry family.
N/A = No suitable options available postemergence.

The invention claimed is:

1. A method of controlling aryloxy alkanoate dioxygenase 12 (AAD-12) dicot soybean volunteer plants in a field comprising monocot plants, said soybean volunteer plants comprising Event DAS-68416-4 as available in seed deposited under ATCC deposit number PTA10442, said soybean volunteer plants comprising an AAD-12 gene that encodes an AAD-12 protein, wherein said method comprises
applying a herbicide to said soybean volunteer plants.

2. The method of claim 1, wherein said monocot plants are corn plants.

3. The method of claim 1, wherein said herbicide is selected from the group consisting of dicamba, clopyralid, and a triazine.

4. The method of claim 1, wherein said triazine herbicide is atrazine.

5. The method of claim 1, wherein said monocot plant comprises a glyphosate- and/or a glufosinate-tolerance gene.

6. The method of claim 1, wherein said volunteer plants further comprise a glyphosate-tolerance gene, and said herbicide is selected from the group consisting of dicamba, clopyralid, and a triazine.

7. The method of claim 1, wherein said herbicide is glyphosate.

* * * * *